United States Patent
Yu

(10) Patent No.: US 8,687,204 B2
(45) Date of Patent: Apr. 1, 2014

(54) METHOD AND APPARATUS FOR MEASURING REFRACTIVE INDEX BASED ON A RATIO BETWEEN A NUMBER OF SECOND FRINGES DIVIDED BY A DIFFERENCE OF THE NUMBER OF SECOND FRINGES MINUS A NUMBER OF FIRST FRINGES

(75) Inventor: Chung-Chieh Yu, Tucson, AZ (US)

(73) Assignee: Canon Kabushiki Kaisha, Tokyo (JP)

( * ) Notice: Subject to any disclaimer, the term of this patent is extended or adjusted under 35 U.S.C. 154(b) by 386 days.

(21) Appl. No.: 13/071,383

(22) Filed: Mar. 24, 2011

(65) Prior Publication Data

US 2012/0243002 A1    Sep. 27, 2012

(51) Int. Cl.
    *G01N 21/41*    (2006.01)

(52) U.S. Cl.
    USPC .......................................... 356/517

(58) Field of Classification Search
    USPC .................................. 356/450–521
    See application file for complete search history.

(56) References Cited

U.S. PATENT DOCUMENTS

| | | | | |
|---|---|---|---|---|
| 5,034,617 | A * | 7/1991 | Isobe | 250/559.28 |
| 5,526,118 | A * | 6/1996 | Miyagawa et al. | 356/484 |
| 5,557,408 | A * | 9/1996 | Kanaya | 356/514 |
| 5,909,282 | A * | 6/1999 | Kulawiec | 356/504 |
| 5,943,134 | A * | 8/1999 | Yamaguchi et al. | 356/503 |
| 5,999,262 | A * | 12/1999 | Dobschal et al. | 356/504 |
| 6,327,039 | B1 | 12/2001 | Groot et al. | |
| 6,330,065 | B1 | 12/2001 | Hill | |
| 6,441,907 | B1 | 8/2002 | Son et al. | |
| 6,545,763 | B1 | 4/2003 | Kim et al. | |
| 7,130,060 | B2 | 10/2006 | Bornhop et al. | |
| 7,663,765 | B2 | 2/2010 | Yuan | |
| 2002/0131053 | A1 | 9/2002 | Groot et al. | |
| 2002/0140945 | A1 | 10/2002 | Groot et al. | |
| 2002/0140946 | A1 | 10/2002 | Groot et al. | |
| 2006/0012800 | A1 * | 1/2006 | Bornhop et al. | 356/517 |
| 2009/0161114 | A1 | 6/2009 | Yuan | |

OTHER PUBLICATIONS

Shumate Michael Stewart, "An Interferometric Measurement of Index of Refraction," California Institute of Technology; Pasadena, CA, Mar. 13, 1964, pp. 1-75.

* cited by examiner

*Primary Examiner* — Tarifur Chowdhury
*Assistant Examiner* — Michael P Lapage
(74) *Attorney, Agent, or Firm* — Canon USA Inc. IP Division

(57) ABSTRACT

A method and apparatus for measuring refractive index of an object are disclosed. The method includes, acquiring a number of first fringes of a first interference pattern formed by interference of a first beam of light transmitted through the object with a second beam of light not transmitted through the object; acquiring a number of second fringes of a second interference pattern formed by interference of a third beam of light reflected from a first surface of the object with a fourth beam of light transmitted through the object and reflected from a second surface of the object; and calculating the refractive index of the object based on the number of first fringes and the number of second fringes. The method may further include calculating the Abbe number of the object based on the refractive indices of the object measured at different wavelengths.

23 Claims, 9 Drawing Sheets

| Wavelength | # | #' | n |
|---|---|---|---|
| 632nm | 105 | 425 | 1.3281 |
| 632nm | 105 | 425 | 1.3281 |
| 632nm | 105 | 425 | 1.3281 |
| 632nm | 105 | 424 | 1.3292 |
| 632nm | 105 | 425 | 1.3281 |
| 543nm | 123 | 494 | 1.3315 |
| 543nm | 123 | 494 | 1.3315 |
| 543nm | 123 | 494 | 1.3315 |
| 543nm | 123 | 495 | 1.3306 |
| 543nm | 123 | 495 | 1.3306 |

FIG. 11

| | 1 | 2 | 3 | 4 | 5 | mean | sigma |
|---|---|---|---|---|---|---|---|
| # = 100  #' = | 402 | 401 | 401 | 401 | 401 | | |
| n = | 1.331 | 1.332 | 1.332 | 1.332 | 1.332 | 1.3318 | 0.0004 |
| # = 1000  #' = | 4016 | 4016 | 4015 | 4015 | 4015 | | |
| n = | 1.3316 | 1.3316 | 1.3317 | 1.3317 | 1.3317 | 1.33166 | 0.00005 |
| #' = | 4015.6 | 4015.6 | 4015.4 | 4015.7 | 4015.5 | | |
| n = | 1.33161 | 1.33161 | 1.33163 | 1.33160 | 1.33162 | 1.33161 | 0.00001 |

Runs

Fringes counted to one digit after decimal point

METHOD AND APPARATUS FOR MEASURING REFRACTIVE INDEX BASED ON A RATIO BETWEEN A NUMBER OF SECOND FRINGES DIVIDED BY A DIFFERENCE OF THE NUMBER OF SECOND FRINGES MINUS A NUMBER OF FIRST FRINGES

FIELD

The disclosure of this application relates generally to optical metrology, and in particular to a method and apparatus suitable for measurements of refractive index.

BACKGROUND

Accurate knowledge of the refractive index of materials is very important and useful in many fields of technology. For example, the refractive index can be used to determine substance composition for chemical analysis; it is used in the design of optical systems that include refracting elements to optimize imaging quality; and it may also be used for material identification and characterization, among others. For optical materials, the refractive index is generally defined as the ratio of the speed of light in vacuum to that in the material itself. Although refractive index data is readily available for almost any known transparent or crystalline material, it is usually given for only one or a few wavelengths of the electromagnetic spectrum. In addition, the refractive index of a given material may vary in the presence of externally applied magnetic or electric fields, or the temperature of the material, among others. Accordingly, there is a need to more accurately measure the index of refraction of materials.

A variety of instruments and techniques for determining the refractive index of materials are currently available. Among those, interferometry is a well known technique for measuring the refractive index of a substance. The measurement of refractive index using a two-beam interferometer may be accomplished by placing a sample of known thickness in one of the beams and determining the change in the order of the interference fringes. Representative examples of conventional interferometry are discussed below.

Kim et al., U.S. Pat. No. 6,545,763 (hereafter "Kim"), discloses a method for measuring a thickness profile and a refractive index using white-light scanning interferometry. Kim discloses using white light to perform low coherence interferometry to measure the phase graph (phase delay profile along the z-direction of a sample); extracting a mathematical phase graph through modeling of a measurement object; and estimating the sample thickness and refractive index by minimizing the difference between measured and simulated phase graphs. However, because the refractive index is a function of the wavelength of light, using white light as the light source does not provide an absolute and accurate measurement. In addition, the phase profile measured along the z-direction of the sample depends on both the physical movement and the sample refractive index. Therefore, the accuracy of the index measurement depends on the accuracy of the z-movement measurement.

Bornhop et al., U.S. Pat. No. 7,130,060 (hereafter "Bornhop"), discloses a technique for refractive index determination by micro interferometric reflection detection. Bornhop discloses placing a sample of interest (liquid) into a capillary tube with a known physical configuration. The known refractive index of the capillary tube is used as a reference for the liquid sample. Therefore, a precise knowledge of the refractive index of the capillary is required for determining the refractive index of the liquid. In other words, the accuracy of the liquid index measurements is limited by the accuracy of the knowledge of the refractive index of the capillary tube which acts like an "index reference." This greatly limits the accuracy of this technique.

Kun-I Yuan, U.S. Pat. No. 7,663,765 (hereafter "Yuan"), discloses a refractive-index measurement system that measures a "change" in refractive index of a lens placed inside a container. The container accommodates the lens therein and is filled with a medium having a refractive index substantially the same as a theoretical refractive index of the lens. Interference fringes of a first light beam transmitted through different points (a first point and a second point) of the sample and a second light beam not transmitted through the sample are counted. The change of refractive index of the lens is obtained by comparing the value of refractive index of the lens at the second point with the theoretical refractive index of the lens at the first point. Yuan does not disclose how to measure the absolute refractive index, but only a relative change in refractive index. Moreover, according to Yuan, the accuracy of the measurement relies on the assumption that the medium in which lens is placed has a refractive index substantially the same as a theoretical refractive index of the lens.

What is needed, therefore, is a technique for reliably and accurately measuring the refractive index of a sample in a simple and efficient manner.

SUMMARY

In accordance with at least one disclosed example, the instant disclosure provides a novel method and apparatus suitable for measuring refractive index of a sample using interferometry.

According to one aspect of the present invention, a method for measuring refractive index of an object includes, acquiring a number of first fringes of a first interference pattern formed by interference of a first beam of light transmitted through the object with a second beam of light not transmitted through the object; acquiring a number of second fringes of a second interference pattern formed by interference of a third beam of light reflected from a first surface of the object with a fourth beam of light transmitted through the object and reflected from a second surface of the object; and calculating the refractive index of the object based on the number of first fringes and the number of second fringes.

According to another aspect of the present invention, an apparatus for measuring the refractive index of an object includes, a light source that generates a first beam of light having a first optical path and a second beam of light having a second optical path different from the first optical path; an object holder that holds the object in one of the first and second optical paths such that a portion of the one of the first and second optical paths passes through the object; a first optical combiner that combines the first beam with the second beam to form a first interference pattern; the light source further generating a third beam of light and a fourth beam of light, the third beam of light being reflected from a first surface of the object without being transmitted through the object, and the fourth beam of light being transmitted through the object and reflected from a second surface of the object; a second optical combiner that combines the third beam with the fourth beam to form a second interference pattern; a fringe counter that counts a number of first fringes of the first interference pattern and a number of second fringes of the second interference pattern; and a processing device that calculates the refractive index of the object based on the number of first fringes and the number of second fringes.

According to yet a further aspect of the present invention, the Abbe number of an object can be calculated based on the refractive index of the object measured at different wavelengths.

Other modifications and/or advantages of present invention will become readily apparent to those skilled in the art from the following detailed description in reference to the attached drawings.

BRIEF DESCRIPTION OF THE DRAWINGS

FIG. 11 illustrates an exemplary summary of experimental results obtained with a refractive index measuring method and apparatus in accordance with the present invention.

DETAILED DESCRIPTION

Figure 1:
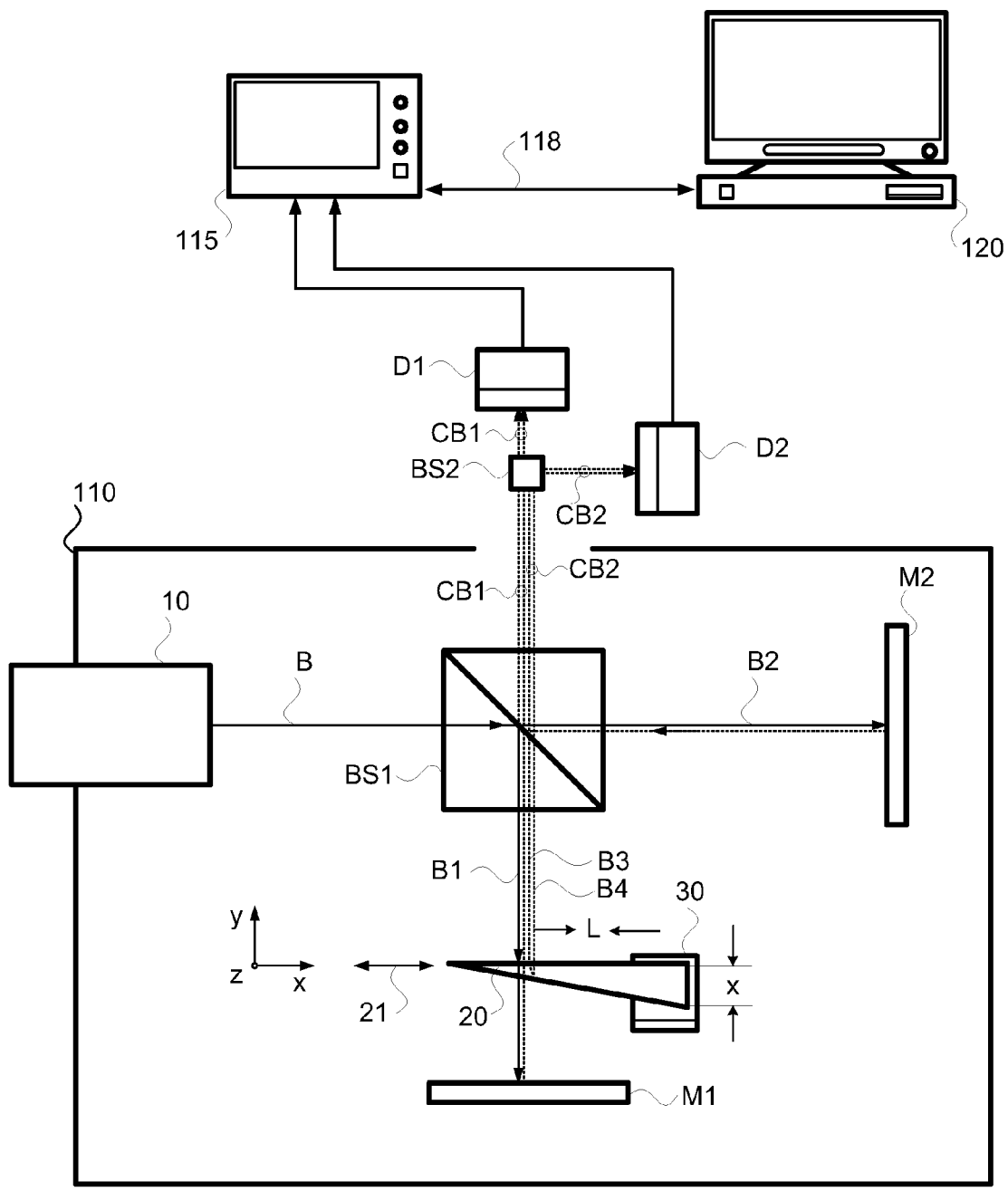
FIG. 1 illustrates an exemplary arrangement of a refractive index measuring apparatus in accordance with the present invention.

In the following description, reference is made to the accompanying drawings which are illustrations of embodiments in which the disclosed methods and apparatus may be practiced. It is to be understood, however, that those skilled in the art may develop other structural and functional modifications without departing from the novelty and scope of the instant disclosure. As used herein, the term "interference" generally refers to the addition (superposition) of at least two waves (e.g., light waves) that results in a new wave pattern (e.g., fringe pattern). Using the concept of wave optics, therefore, the term "fringe" or "fringes" refers to concentric period patterns produced by the interference of two or more light waves.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage device such as a magnetic or optical disk and disk drive for storing information and instructions, an optional user output device such as a display device (e.g., a monitor) for displaying information to the computer user, an optional user input device including alphanumeric and function keys (e.g., a keyboard) for communicating information and command selections to the processor, and an optional user input device such as a cursor control device (e.g., a mouse or pointing device) for communicating user input information and command selections to the processor.

As will be appreciated by those skilled in the art, the present examples may be embodied as a system, method or tangible computer program product. Accordingly, some examples may take the form of an entirely hardware embodiment, and entirely software embodiment (including firmware, resident software, micro-code, etc.) or an embodiment combining software and hardware aspects that may all generally be referred to herein as a "circuit", "module" or "system". Further, some embodiments may take the form of a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored on computer-readable media that when read by a computer can direct the computer or other programmable data processing apparatus to function in a particular manner to implement the function/act/step specified in the flowchart and/or block diagram. Referring now to the drawings, where like reference numerals refer to like parts, exemplary embodiments of the invention are described.

FIG. 1 is a diagram that illustrates an arrangement of a refractive index measuring apparatus 100 according to an embodiment of the present invention. In its simplest form, the refractive index measuring apparatus 100 includes an interferometer 110 (e.g., a Michelson interferometer), one or more detectors D1 & D2, and a spectrum analyzer 115 optionally connected to a data processing device 120 via a network connection 118. The processing device 120 and the spectrum analyzer 115 can be combined into a single unit, such as a general purpose computer equipped with hardware and software configured to receive electric signals from at least one of detectors D1 D2, convert the electric signals into digital data and process the data to produce a visual or audible output.

From a light source 10 of the interferometer 110, a beam of light B is split by a beam splitter BS1 into a first beam B1 reflected from the beam splitter BS1 and a second beam B2 transmitted through the beam splitter BS1; the first beam B1 and the second beam B2 are preferably of substantially equal amplitudes. The first beam B1 and second beam B2 continue to a first mirror M1 and a second mirror M2, respectively, where the directions of beams B1 and B2 are reversed. After being reflected from mirrors M1 and M2, respectively, the first beam B1 and the second beam B2 come together at the beam splitter BS1 and leave the interferometer as a first combined beam CB1. Thus, the resulting beam CB1 now includes rays that have traveled separate optical paths, and— if the rays striking mirrors M1 and M2 are normal or substantially normal to the mirrors—the rays included in beam CB1 can generate an interference pattern (fringes). The beam splitter BS1 therefore essentially acts as both a splitter and an optical combiner (first optical combiner) for the first beam B1 and the second beam B2.

At least one of the mirrors (but preferably both) is equipped with a tilting adjustment mechanism, such as tilting adjustment screws (not shown), that enable adjustment of the first beam B1 or second beam B2 to allow the first beam B1 and the second beam B2 to intersect on the beam splitter BS1. In addition, at least one of the mirrors M1 and M2 may be movable along the direction of the beam incident thereupon, e.g., by means of a sliding guide and micrometer screw (also not shown). Moreover, the beam splitter BS1 may also equipped with a tilting adjustment mechanism. In this manner, the difference between the optical paths of the first beam B1 and the second beam B2 can be adjusted at convenience; and the second beam B2 can be adjusted to overlap the first beam B1 to create the interference. To use the nomenclature of a conventional interferometer, the part of the interferometer containing the first beam B1 and first mirror M1 (bottom part of interferometer 110) will be referred to as the signal arm, and the part of the interferometer containing the second beam B2 and second mirror M2 (right-hand side of interferometer 110 in FIG. 1) will be referred to as the reference arm.

A sample 20 of a predetermined length and a varying thickness x (e.g., a wedge-shaped sample) is inserted in the signal arm (i.e., in the optical path of the first beam B1) of interferometer 110. The sample 20 may alternately be inserted in the optical path of the second beam B2, in which case, the signal and reference arms of interferometer 110 would be reversed. The sample 20 is preferably held by a positioning stage 30 (object holder), so that sample 20 can be positioned and aligned. In addition, sample 20 (or stage 30) is moved by a moving means such as a step motor or the like (not shown), such that sample 20 is translated. More specifically, sample 20 is moved a predetermined distance L along a direction 21 which is substantially perpendicular to the first beam B1 incident upon the sample 20. In this manner, the first beam B1 is now twice transmitted through the variable thickness x of sample 20 before recombining with the second beam B2 at the beam splitter BS1. That is, a portion of the optical path of the first beam B1 includes a distance equal to the thickness x that the first beam B1 travels through the sample 20. As a result, the sample 20 introduces a phase delay to the first beam B1.

The phase delay introduced by the sample 20 is position dependent. That is, varying the position of the sample 20 with respect to the first beam B1 by a predetermined distance L causes the length of the first beam B1 that passes through the sample 20 to change according to the varying thickness x of the sample 20. Thus, depending on the position of the sample 20 with respect to the first beam B1, the interference of the phase-delayed first beam B1 with respect to the second beam B2 will generate interference fringes. The number of fringes caused by the variation in length of the optical path of the first beam B1 is counted whilst the sample 20 is moved in a direction substantially perpendicular to the first beam B1. The interference fringes are detected by detector D1 or detector D2 (fringe detectors); these fringes can be observed and counted at the analyzer 115 while the sample 20 is being translated by a not-shown micrometer step-motor or the like that makes up part of a positioning stage 30. The detector D1 or D2 may include, for example, a single-point photodetector such as a photodiode, a charge-coupled device (CCD) or a complementary metal-oxide-semiconductor (CMOS) sensor, or the like. The analyzer 115 displays and counts the number of fringes, which are stored in—and subsequently used by—the processing device 120 or the analyzer 115 to determine the index of refraction of the sample 20.

As stated above, the sample 20 is monotonically and repetitively translated in a direction substantially perpendicular to the first beam B1 by an amount L. In other words, the position of the first beam B1 on sample 20 is changed by the amount L, whereby the thickness x of the sample 20, and therefore the optical path of the first beam B1, monotonically change and a number of first fringes are generated and observed (counted) while the sample is moved. Naturally, instead of moving the sample, it is possible that the first beam B1 be monotonically and repetitively translated in a direction substantially perpendicular to the sample 20 by an amount L, whereby the thickness x of the sample 20 traversed by the first beam B1, and therefore the optical path of the first beam B1, monotonically change and the number of first fringes are generated and observed while the first beam B1 is moved. In the case that the beam is moved with respect to the sample, a scanning or step-wise movement technique may be adopted to move the beam. Therefore, regardless of whether the sample or the beam move, it can be generally said that a number of first fringes can be generated and counted while the position of the sample 20 with respect to the first beam B1 (or the position of the first beam B1 on the sample 20) is monotonically and repetitively changed in a direction substantially perpendicular to each other by an amount L.

Specifically, a first fringe is generated when the "optical path length" experienced by the first beam B1 is changed by $\lambda$, where $\lambda$ is the wavelength of the light being used. The change in the optical path length is given by $(2*\Delta x*n_s)-(2*\Delta x*n_e)$, where 2 represents the double pass of first beam B1 through the sample 20, $\Delta x$ is the change in sample 20 thickness due to the translation (movement) of sample 20, $n_s$ is the refractive index of the sample 20, and $n_e$ is the refractive index of the environment or medium (e.g., gas or liquid) which the sample 20 is in. Ideally, the sample 20 is in vacuum and $n_e$ is 1. In practice, however, the sample 20 can be in the air and $n_e$ is approximately 1.0008 in this case. Therefore, the thickness change ($\Delta x$), which generates one fringe, is equal to $\lambda/2*(n_s-n_e)$. When the sample 20 is translated such that the position of the first beam B1 on the sample 20 is changed by the amount of L, the total sample thickness change, x, can be expressed as L/A.R., where A.R. is the aspect ratio of the sample 20. Accordingly, the number of first fringes # can be determined by taking the ratio between x and $\Delta x$, which is represented in Eq. (1), as follows:

$$\#=(n_s-n_e)*(L/A.R.)*2/\lambda \qquad \text{Eq. (1).}$$

In the foregoing example of generating and counting a number of first fringes (#), the use of a wedged sample has been described. Those of ordinary skill in the art may appreciate, however, that the shape of the sample is not necessarily limited to a wedge. As long as the number of fringes can be accurately detected and counted, a substantially parallel sample, such as a thin film (solid or liquid), a waveplate or the like, may also used. Specifically, in the derivation of Eq. (1) above, the change in sample 20 thickness ($\Delta x$) due to the translation (movement) of sample 20 has been premised on the assumption that sample 20 wedge-shaped and has a varying thickness. However, the change in sample thickness ($\Delta x$) due to the translation (movement) of sample may also be representative (or indicative) of irregularities in the thickness of a substantially parallel sample. That is, the change in sample thickness ($\Delta x$) due to the translation (movement) of sample can be of morphological features in the surface of a sample. In this manner, for example, when a surface of a thin waveplate sample or a semiconductor substrate is coated with certain patterns, fringes indicative of the presence and thickness of such patterns can be detected. It is a matter of course therefore that the change in sample thickness (Δx) due to the translation of sample may be obtained in many other ways, so that the sample is not limited to a wedge-shaped sample. For example, a rectangular parallelepiped sample or cubic sample may be used. The movement of the sample may include rotation or vibration of the sample—in addition to or in combination with translation.

Once the number of first fringes is obtained by the interference of the first beam B1 and the second beam B2, the refractive index of sample 20 could be deduced using Eq. (1) if L, A.R. and λ were known. Generally, if a coherent light source, such as a laser is being used in apparatus 100, the wavelength λ can be known a priori. However, L and A.R. are difficult to determine. Moreover, even when L and A.R. can be determined, these values tend to be inaccurate due to difficulties in repeatability. Accordingly, if the distance L, the aspect ratio A.R., or the wavelength λ are not known, the absolute refractive index cannot be obtained from the number of first fringes. Nevertheless, a "relative" refractive index or a "change" in refractive index of the sample 20 can still be obtained by using the number of first fringes and a number of second fringes counted with the above described apparatus 100.

A relative refractive index of a given sample (test sample) can be estimated, by measuring the ratio of two refractive indices of two samples. Specifically, a first number of fringes $\#_{ref}$ of a reference sample (first sample) can be obtained, by placing a sample of a known refractive index $n_{ref}$ in the measuring apparatus 100 and obtaining the number of first fringes in the manner described above. A number of second fringes $\#_{tst}$ of a test sample (second sample) can be obtained, by placing the test sample of equal dimensions and shape, but of unknown refractive index $n_{tst}$, in the measuring apparatus 100, and performing the measurement to obtain a number of second fringes $\#_{tst}$. The relative refractive index $n_{tst}$ of the test sample can be simply calculated by obtaining a ratio of the number of first fringes $\#_{ref}$ to the number of second fringes $\#_{tst}$, and multiplying the ratio by the known refractive index $n_{ref}$ of the reference sample. That is, $n_{tst}=(\#_{tst}/\#_{ref})*n_{ref}$. However, the reference sample must have a shape and dimensions exactly the same as the shape and dimensions of the test sample. And, both the repeatability of the sample movement and the accuracy of the reference refractive index $n_{ref}$ will affect the accuracy of the newly found refractive index $n_{tst}$.

A change in refractive index of a given sample can be measured, by obtaining the above-described number of first fringes and number of second fringes on the same sample, but under different conditions. For example, a number of first fringes can be obtained by performing the measurement at a first temperature; and a number of second fringes can be obtained at a second temperature. Alternatively, a number of first fringes can be obtained by placing a sample (e.g. a lens, waveguide, wafer) under a first (normal) stress and performing the measurement; and a number of second fringes can be obtained by placing the sample under a second stress (external force or pressure) and performing the measurement with measurement apparatus 100, as described above. From the number of first and second fringes, a change in the refractive index can be obtained, for example, in a manner as disclosed by Yuan in U.S. Pat. No. 7,663,765, which is incorporated herein by reference. However, the measurement of a mere "change" in refractive index may not satisfy the necessity to know the absolute refractive index of a sample. In addition, the lack of repeatability in sample movement will affect the accuracy of the measurement results.

To measure the "absolute" refractive index of a given sample (object), the sample should ideally be placed in a vacuum, so that all sources of uncertainty, such as variation of temperature and inaccuracies in the refractive index of the environment are eliminated. However, measuring the refractive index of a sample in vacuum may prove to be excessively costly and may not accessible to most practical situations. Thus, in accordance with at least one embodiment of the present invention, the refractive index of the sample is measured with respect to the refractive index of the environment (medium) where the sample is in. In most cases, the environment or medium is air which has a refractive index of approximately 1.0008. In other cases, a sample may be placed in a gas or liquid contained in a transparent vessel, in which case, the refractive index of the medium and the vessel should be taken into consideration. However, in order to remove uncertainties introduced by environmental conditions, the refractive index of the sample is measured twice and these measurements are compared to obtain what may be perceived as a pseudo "absolute" refractive index. Preferably, in both instances the refractive index of the sample should be measured while maintaining the sample under the same environmental conditions. In this manner, any type of uncertainty due to changes in temperature or changes in reference values can be removed. To that end, a number of first fringes # (first measurement) and a number of second fringes #' (second measurement) should be obtained from the sample, preferably under the same conditions and probing the same area of the sample. In accordance with the present invention, a first measurement of the interference between the first beam B1 and the second beam B2—in the manner described above—is performed to acquire the number of first fringes. A number of second fringes is acquired by measuring a second interference pattern formed by the interference between a third beam B3 reflected from a first surface 20A of the sample 20 and a fourth beam B4 reflected from a second surface 20B of the sample 20.

Figure 2A:
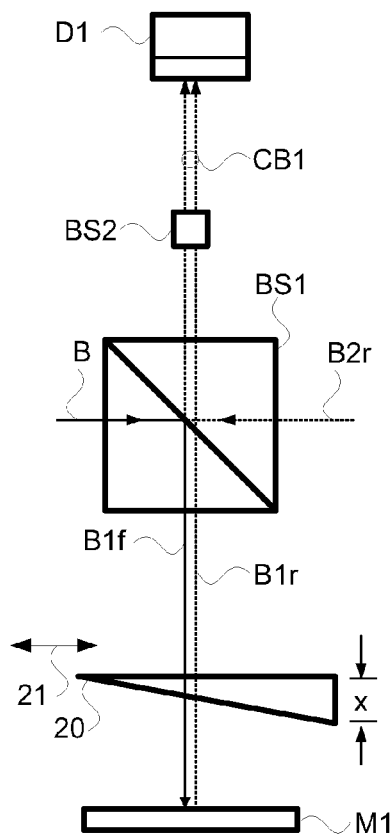
FIGS. 2A through 2C illustrate exemplary arrangements of optical paths of first, second, third and fourth beams in accordance with the present invention.

Specifically, as described above in reference to FIG. 1, the number of first fringes can be detected by detector D1 or detector D2 of apparatus 100. FIG. 2A illustrates one possible arrangement in which the first beam B1 travels in a forward path (B1f) through sample 20, reaches mirror M1 and is reflected in a reflected path (B1r). The second beam B2, on the other hand, arrives at mirror M2 after passing through the beam splitter BS1, and is reflected off from mirror M2 (not shown in FIG. 2A) along a reflected path B2r. Ultimately, the first beam B1 and second beam B2 come together at beam splitter BS1, thereby forming a combined beam CB1. An interference pattern formed by the first beam B1 and second beam B2, while sample 20 is moved in direction 21, is detected by detector D1.

In addition, under the same conditions (e.g., under the same sample temperature and sample movement), a number of second fringes can be obtained. For this, as shown in FIG. 2C, a third beam B3 is reflected off from a first surface 20A and a fourth beam B4 is reflected off from a second surface 20B of sample 20. The third beam B3 and fourth beam B4, after reflecting off the first surface 20A and the second surface 20B, respectively, also come together at beam splitter BS1 to form a combined beam CB2 (shown in FIG. 1). Thus, a number of second fringes can be acquired under the same conditions as the first fringes (e.g., probing the same region of the sample) while the sample 20 is being moved in the manner above described. Since the beam splitter BS1 also serves to combine the third beam B3 and the fourth beam B4, it can be said that beam splitter BS1 acts as a second optical combiner.

However, the third and fourth beams may alternately be combined to form the combined beam CB2 by using other optical elements as described more in detail below.

Figure 2B:
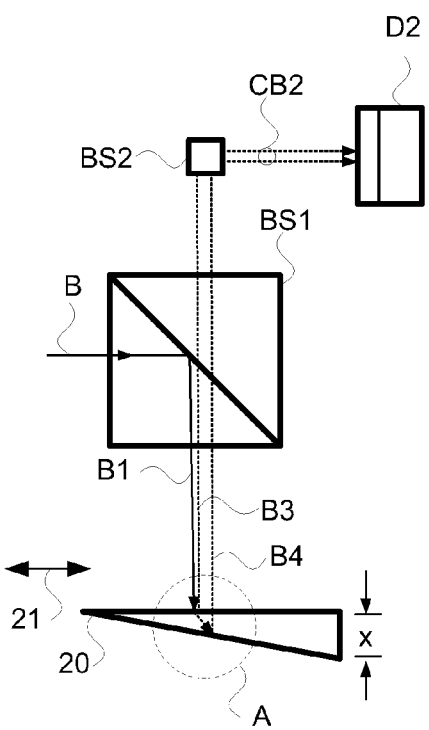
Figure 2C:
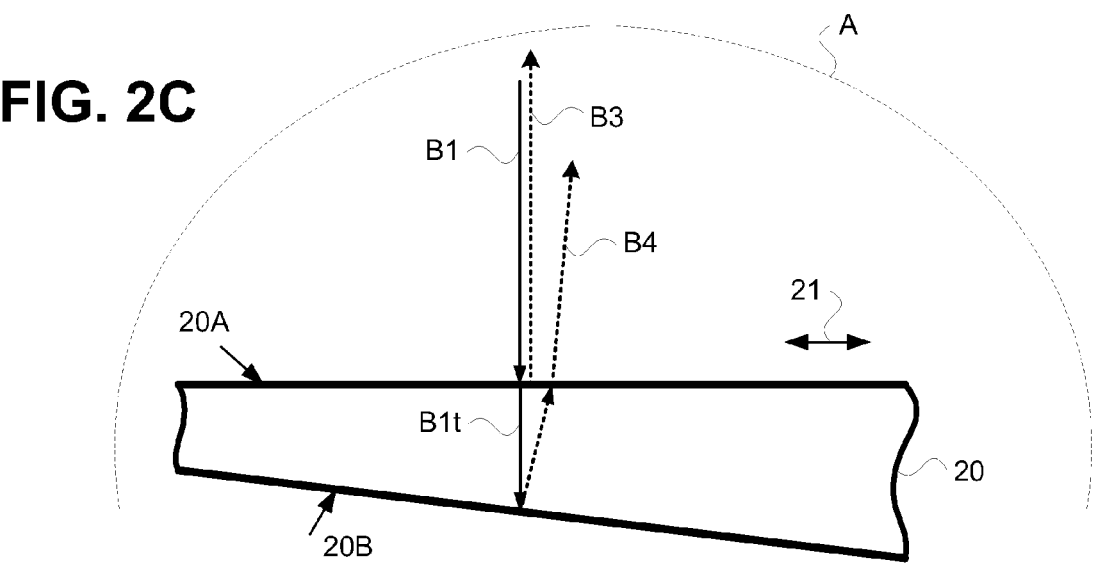

FIG. 2B illustrates an arrangement in which, when the first beam B1 is incident upon sample 20, a third beam B3 and a fourth beam B4 can be generated by reflecting part of the firs beam B1 off of a first surface 20A (front surface) and a second surface 20B (back surface), respectively. More specifically, as it is known to a person having ordinary skill in the art, when an incident beam of light having an angle $\theta_i$ (other than the critical angle) with respect to the normal to a plane separating two optically transparent media having refractive indices $n_1$ and $n_2$, respectively, the incident beam is partially reflected at an angle $\theta_r = \theta_i$ with respect to the normal and is partially transmitted at an angle $\theta_t$, such that $n_1 \sin \theta_i = n_2 \sin \theta_t$, as established by Snell's Law.

In the present embodiment, when a beam of light interacts with sample 20, Snell's Law can be repeatedly applied at each surface on which the beam interacts with sample 20. More specifically, as previously described in reference to FIG. 1, the first beam B1 is transmitted through sample 20, reaches the mirror M1, and is reflected therefrom towards the beam splitter BS1. However, not all of the light of the first beam B1 is transmitted through the sample 20. Indeed, as illustrated in FIG. 2B (where area A shown in detail in FIG. 2C), a first part of the first beam B1 is reflected from a first surface 20A of sample 20, thereby forming a third beam B3. In addition, another part of the first beam B1 (part B1t) is transmitted through the variable thickness x of the sample 20 and is reflected off from the second surface 20B, thereby forming the fourth beam B4. The forming of the third beam B3 and the fourth beam B4 is not limited to the interactions (reflection/refraction) of the first beam B1 with sample 20. Instead of using the first beam B1, an additional beam B11 (as shown in FIG. 3) having an optical path substantially parallel to the optical path of the first beam B1 can be made incident upon sample 20.

Figure 3:
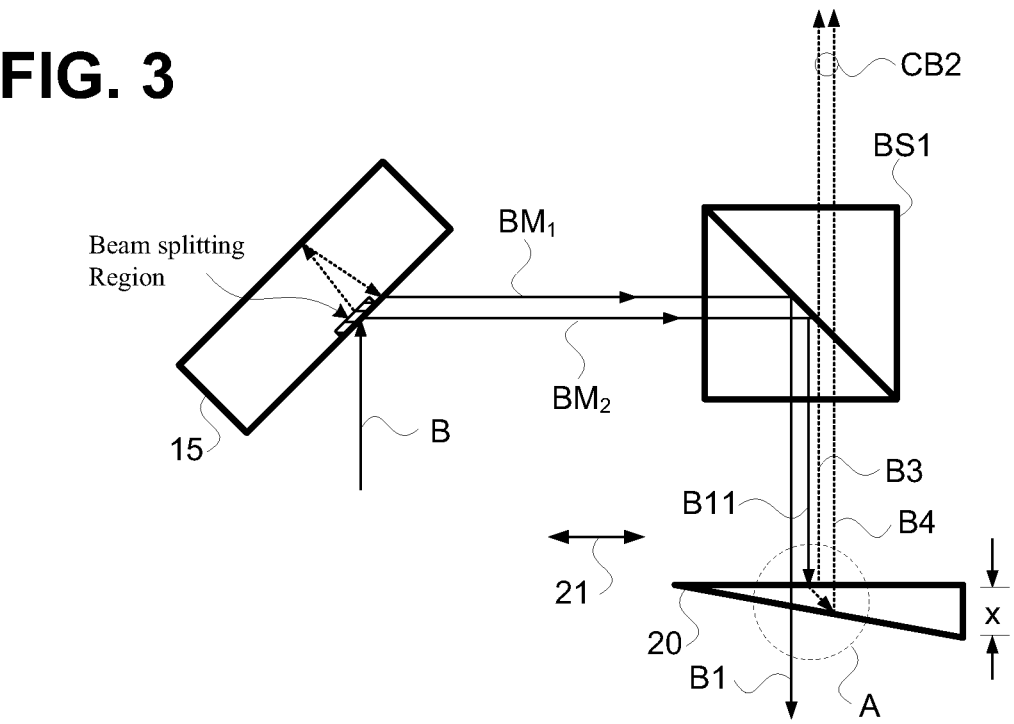
FIG. 3 illustrates an exemplary arrangement of how the first, second, third and fourth beams can be generated with a single wavelength in accordance with the present invention.

More specifically, FIG. 3 illustrates another arrangement of apparatus 100 according to the first embodiment of the present invention. In the arrangement of FIG. 3, the beam of light B generated by light source 10 (in FIG. 1) can be first divided into plural beams of light $BM_1$ and $BM_2$. For this, a beam splitter device 15, such as a Jamin plate or a prism can be used. The beams $BM_1$ and $BM_2$ are preferably of the same intensity, and having been generated by a single light source, these beams preferably have the same wavelength. Each of beams $BM_1$ and $BM_2$ are then guided towards the beam splitter BS1. At beam splitter BS1, in turn, beam $BM_1$ is split into first beam B1 and second beam B2, as shown and described above in reference to FIG. 1. On the other hand, the beam $BM_2$ becomes beam B11 which is made to interact with the first surface 20A and the second surface 20B of sample 20 in the manner described above in reference to FIGS. 2B and 2C.

Figure 4:
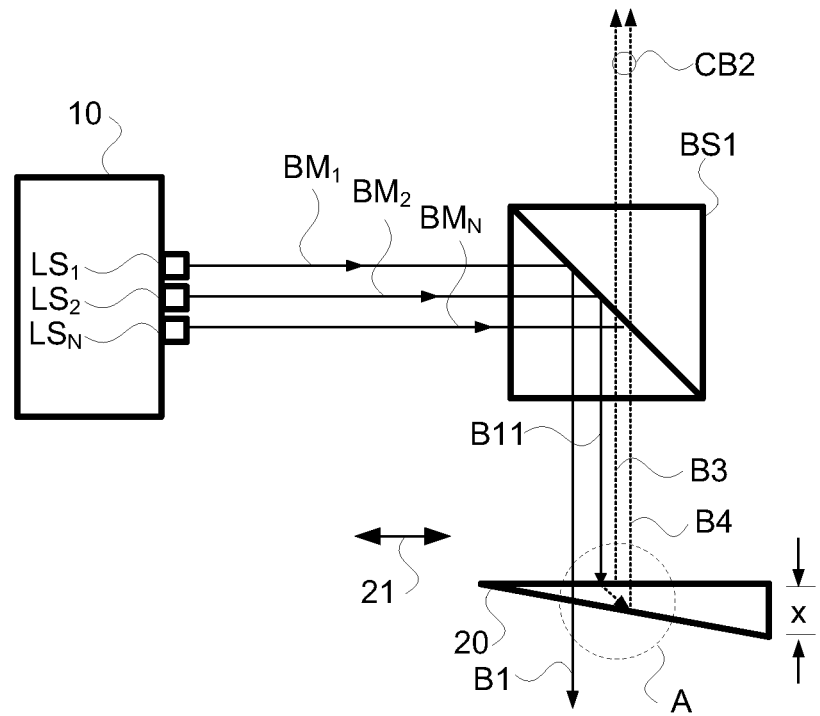
FIG. 4 illustrates an exemplary arrangement of how the first, second, third and fourth beams can be generated with a plurality of wavelengths in accordance with the present invention.

FIG. 4 illustrates a further arrangement of apparatus 100 according to the first embodiment of the present invention. In the arrangement of FIG. 4, light source 10 includes a plurality of light emitting elements $LS_1, LS_2 \ldots LS_n$. Accordingly, an equal amount of light beams $BM_1, BM_2, \ldots, BM_n$ can be generated from light source 10, whereby each of beams $BM_1, BM_2, \ldots, BM_n$ can function essentially as a source for a separate interferometer overlapped onto each other. This arrangement is considered of particular interest for simultaneous (or concurrent) refractive index measurements that can provide highly accurate results in a very simple and efficient manner. Moreover, when each of the light emitting elements $LS_1, LS_2 \ldots LS_n$ generates a corresponding beam of light at a different wavelength, the measurement results (i.e., the counting of first fringes, second fringes, and n fringes) can be effectively used to calculate not only the absolute refractive index of an object, but also the Abbe number, as described more in detail below.

Referring back to FIG. 2B and area A shown in detail in FIG. 2C, in the present embodiment, regardless of how the third beam B3 and the fourth beam B4 are generated, the third beam B3 and forth beam B4 respectively reflect off from surface 20A and surface 20B of sample 20, and are selectively guided to substantially overlap the optical path (i.e., the trajectory of) the first beam B1. Accordingly, a second interference pattern is formed when the third beam B3 and the fourth beam B4 are joined at beam splitter BS1. Specifically, the third beam B3 reflected off from the first surface 20A of sample 20 is made to substantially overlap with the optical path B1r of the first beam B1 traveling back from mirror M1 to the beam splitter BS1. If the first beam B1 (as shown in FIG. 2A) or the beam B11 (as shown in FIGS. 3 & 4) is incident on sample 20 at an angle substantially perpendicular to the first surface 20A, the third beam B3 and the fourth beam B4 can be reflected off from the first surface 20A and second surface 20B, respectively, in a direction also substantially perpendicular thereof. After reflecting off from first surface 20A and second surface 20B, respectively, the third beam B3 and fourth beam B4 also come together at beam splitter BS1 as a combined beam CB2. The combined third beam B3 and fourth beam B4, upon reaching beam splitter BS1, interfere with each other, thereby forming a second interference pattern. In the present embodiment, the second interference pattern may be detected by detector D2, as shown in FIG. 2B. Alternatively, second fringes—in addition to the first fringes—can be detected by detector D1. For example, if the second fringes are detected under the same conditions as the first fringes, but at different times, both the first and second fringes can be detected by a single detector. Alternatively, even if the first and second fringes are detected at the same time, a single detector can be used to detect the first and second fringes if interference patterns can be efficiently distinguished and separated, for example, by software. Regardless of which detector is used, the number of the second fringes #' of the second interference pattern can then be observed and stored at analyzer 115 and/or processing device 120, as shown in FIG. 1.

Since the number of second fringes are being obtained under the same conditions (and preferably at the same time) as the number of first fringes, the analyzer 115 can be made to overlap the interference patterns being obtained, for example, as shown in FIGS. 8 and 10A-10C. However, as long as the second fringes are obtained (counted) under the same conditions (e.g. under the same temperature and probing the same region of the sample), it may also be possible to measure the second interference pattern (second fringes) at a different time than the first interference pattern (first fringes). In any case, similar to the number of first fringes, the number of second fringes is dependent on the movement and position of sample 20. However, the optical path difference between the third beam B3 and the fourth beam B4 is different from the optical path difference between the first beam B1 and the second beam B2. Accordingly, the number of second fringes (#') is determined as follows. One fringe is generated when the optical path length that the fourth beam B4 experienced "inside" the sample 20 is changed by $\lambda$, where $\lambda$ is the wavelength of the light being used. The change in the optical path length is $(2 * \Delta x * n_s)$, where 2 represents the double pass of the fourth beam B4 through sample 20, $\Delta x$ is the sample 20 thickness change due to the sample 20 translation, and $n_s$ is the refractive index of the sample 20. Therefore, the thickness change ($\Delta x$), which causes the optical path difference in beam B4 to generate one fringe, is equal to $\lambda/2*n_s$. When the sample 20 is translated such that the position of the third beam B3 on sample 20 is moved by the amount L, the total sample thickness change, x, can be expressed as L/A.R., where A.R. is the aspect ratio of the sample 20. Accordingly, the number of second fringes is given by:

$$\#' = n_s * (L/A.R.) * 2/\lambda \qquad \text{Eq. (2)}.$$

Here it should be noted that, similar to the measurement of the first fringes, instead of moving the sample with respect to the incident beam (third beam B3), the incident beam itself can be moved with respect to the beam in a scanning or step-wise manner, so as to change the position of the beam on the sample.

Because the number of first fringes given by Eq. (1) and the number of second fringes given by Eq. (2) are preferably obtained from the sample 20 substantially simultaneously and under the same conditions, a remarkable simplification can be made so that the calculation of the refractive index of the sample can be attained by a simple ratio of the number of fringes. Specifically, in the present invention, when a ratio of the number of second fringes #' divided by the number of first fringes is considered, all of the unknown variables can be ignored because they simply cancel each other out, as follows:

$$\frac{\#'}{\#} = \frac{(n_s)*(L/A.R.)*2/\lambda}{(n_s - n_e)*(L/A.R.)*2/\lambda} = \frac{(n_s)}{(n_s - n_e)} \qquad \text{Eq. (3)}$$

where $n_e$ is the refractive index of the environment which the sample 20 is in. Ideally, the sample 20 is in vacuum and $n_e$ is 1. In practice, however, the sample 20 can be in the air and $n_e$ is approximately 1.0008 in this case. Eq. (3) can then be used to solve for $n_s$, which results in $$n_s = \frac{(\#'/\#)}{[(\#'/\#) - 1]} * n_e. \qquad \text{Eq. (4)}$$

With the above simplified result, it will be readily evident to persons having ordinary skill in the art that no other prior knowledge, such as the travelling distance (L), aspect ratio (A.R.), or light wavelength ($\lambda$) is required for deducing the refractive index $n_s$ of sample 20. All that is required are the measurement results of the number of first fringes # and the number of second fringes #'. The reason for this simplicity is based on the reasoning that by taking the ratio between these two measurements (# and #') which depend on the same set of references (L, A.R., and $\lambda$), the final equation does not depend on any reference. This cancellation is considered to be of utmost significance because it shows that the refractive index of sample 20 can be deduced from Eq. (4) alone. With the sole constraint that the measurements must include at least two concurrent measurements. Specifically, in accordance with at least one embodiment of the present invention, the refractive index of a given sample can be readily obtained by (i) acquiring a number of first fringes of a first interference pattern formed by interference between a first beam of light transmitted through the object and a second beam of light not transmitted through the object, (ii) acquiring a number of second fringes of a second interference pattern formed by interference of a third beam of light reflected from a first surface of the object with a fourth beam of light transmitted through the object and reflected from a second surface of the object, and (iii) calculating the refractive index of the object based on the number of first fringes and the number of second fringes, as long as the number of first and second fringes are measured substantially simultaneously. In this manner, the two concurrent (simultaneously realized) measurements do not inherit the uncertainty coming from the uncertainties of knowing L or A.R., or $\lambda$. This also means that the measurement is self sufficient in determining $n_s$ because no reference is used for calculating the refractive index. Accordingly, this is indeed a technique for measuring the absolute refractive index using reference-less interferometry.

In accordance with the foregoing description, the second measurement is performed preferably simultaneous and under the same conditions as the first measurement. The reason for performing the first and second measurements substantially concurrent and simultaneous is that the refractive index of a material is temperature and wavelength dependent, and the repeatability of sample movement may be difficult. However, if the first and second measurements can be performed substantially under the same conditions—that is, under the same temperature and probing the same region of the sample—the first and second measurements can be performed at different time and possibly even with different apparatuses. For example, the second fringes can be measured after or before the first fringes have been measured. An apparatus used for measuring the second fringes can be different from an apparatus used for the measurement of the first fringes. In case described in FIG. 1, for example, there are two apparatuses (first and second detectors D1 D2) as the first detector D1 can be used for measuring the first fringes, and the second apparatus can be used for measuring the second fringes D2 at the same time, or at the different time. For cases where very precise measurements are not required, or where a rough estimate can satisfy the measurement requirements, at least one condition (e.g., temperature, timing, or sample region being probed) for the first measurement can be different from that condition for the second measurement.

<Measurement Probing Substantially Same Region of Sample>

As set forth above, the measurements of the first and second fringes should be preferably probing the same region of the sample. However, because sample 20 is premised to have a variable thickness x (e.g., it is a wedged sample), the fourth beam B4 may be reflected off from the second surface 20B along an optical path not substantially overlapped with the optical path of the first beam B1. In this circumstance, the fourth beam B4, after reflecting from the second surface 20B, is walked-off from the optical path of the first beam B1 and is guided towards the beam splitter SB1 along an optical path substantially parallel to (but not overlapped with) the optical path of the first beam B1. That is, the fourth beam B4 after traveling through the variable thickness x of the sample 20, and after being reflected from the second surface 20B, travels along an optical path that is substantially parallel to, but walked-off from, the optical path of the reflected first beam B1, as shown in FIG. 5.

Figure 5:
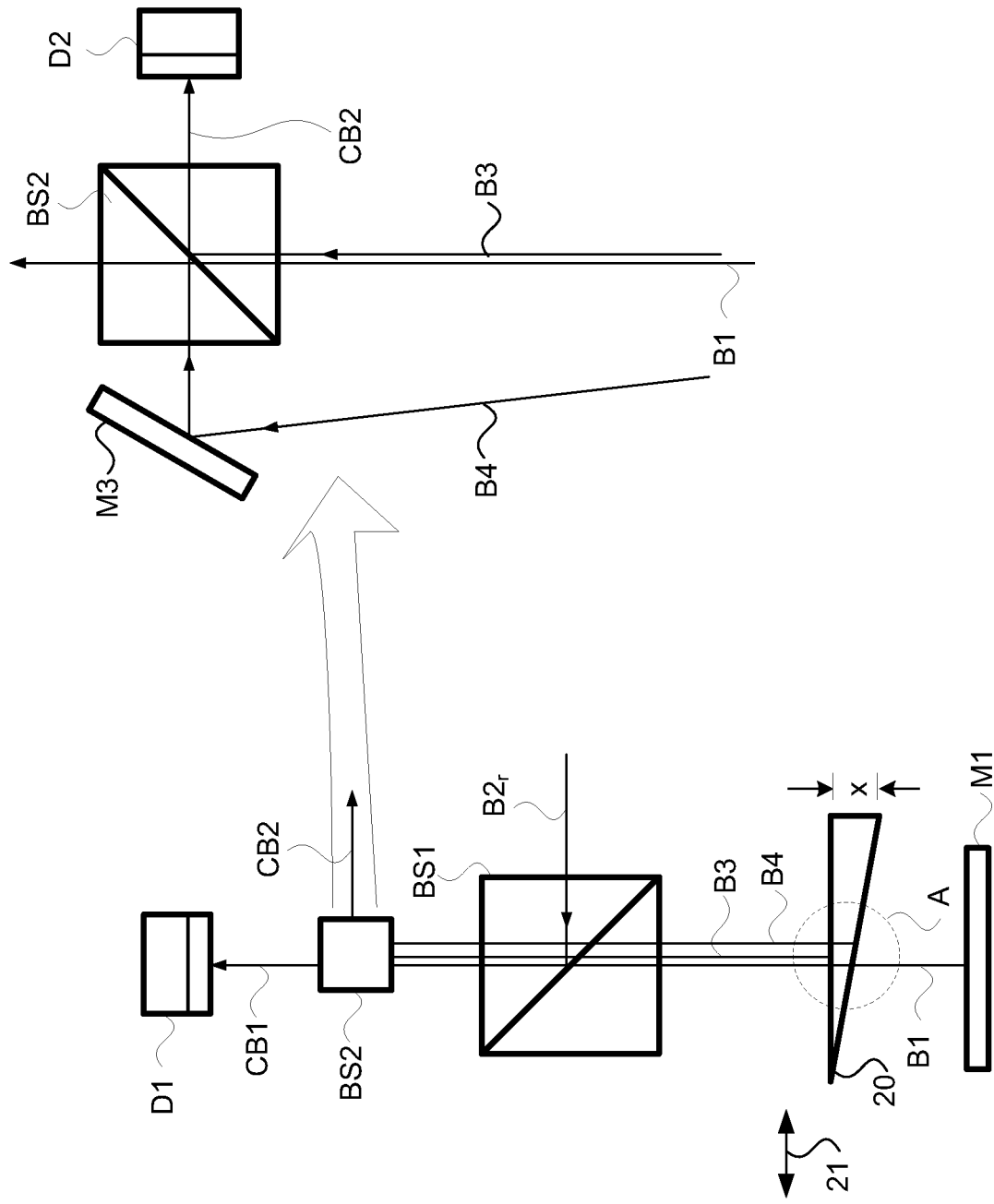
FIG. 5 illustrates an exemplary arrangement of a manner in which the third and fourth beams are selectively aligned with the first and second beams, and a manner in which the third and fourth beams are guided towards a detector thereof.

FIG. 5 illustrates in detail the trajectory (optical path) of the third beam B3 overlapped with that of the first beam reflected (B1) from mirror M1, and the trajectory of the fourth beam B4 walked-off from first beam B1 and third beam B3. Specifically, at the left side of FIG. 5, it is illustrated that the first beam B1, the third beam B3 and the fourth beam B4 travel through beam splitter BS1 towards the beam splitter BS2. However, at the right side of FIG. 5, it is illustrated (with exaggerated detail for ease of illustration) that the fourth beam B4 is walked-off of the path of first and third beams (B1, B3). In this circumstance, the fourth beam B4 needs to be redirected towards the beam splitter BS2 to recombine with another beam at the detector plane. To that end, a third mirror M3 can be placed in the path of the fourth beam B4. With this arrangement, the beam splitter BS2 can effectively pass through the combined beam CB1 (i.e., the first beam B1 combined with the second beam B2), and can combine the third beam B3 with the fourth beam B4, so that the combined beam CB2 is directed to detector D2. In other words, the third beam B3 and the fourth beam B4 are recombined at beam splitter BS2. In addition, beam splitter BS2 serves to separate the combined beam CB1 from the combined beam CB2. Thus, the two pairs of beams (one pair formed by first and second beams; and another pair formed by third beam B3 and fourth beam B4) form two independent signals that can be concurrently measured to obtain the refractive index measurement. The number of second fringes formed by the interference of third beam B3 and fourth beam B4 is detected by the detector D2 and analyzed by analyzer 115 or processing device 120.

In each of the foregoing arrangements, it should be noted that the two measurements, that is, the interference of first beam B1 with the second beam, and the interference of the third beam B3 with the fourth beams B4 may not be probing "exactly" the same area of sample 20. Specifically, as previously noted, due to alignment constraints some beams may be walked-off of the path of another beam. If sample 20 is a homogeneous sample, the walk-off of the beams would have no influence in the accuracy of the measured results. However, when a sample is not homogeneous, it is preferable that the beams strictly follow along a substantially overlapped optical path, so that the same area of the sample is probed. Therefore, the term "overlapped" when used herein to refer to the overlap of beams, means that the two beams should be on top of each other (i.e. the same optical path). Thus, when two beams are overlapped means that the two beams should have an angle between each other of approximately 0 degrees. In the drawings, however, the beams are not overlapped for ease of illustration.

Figure 6:
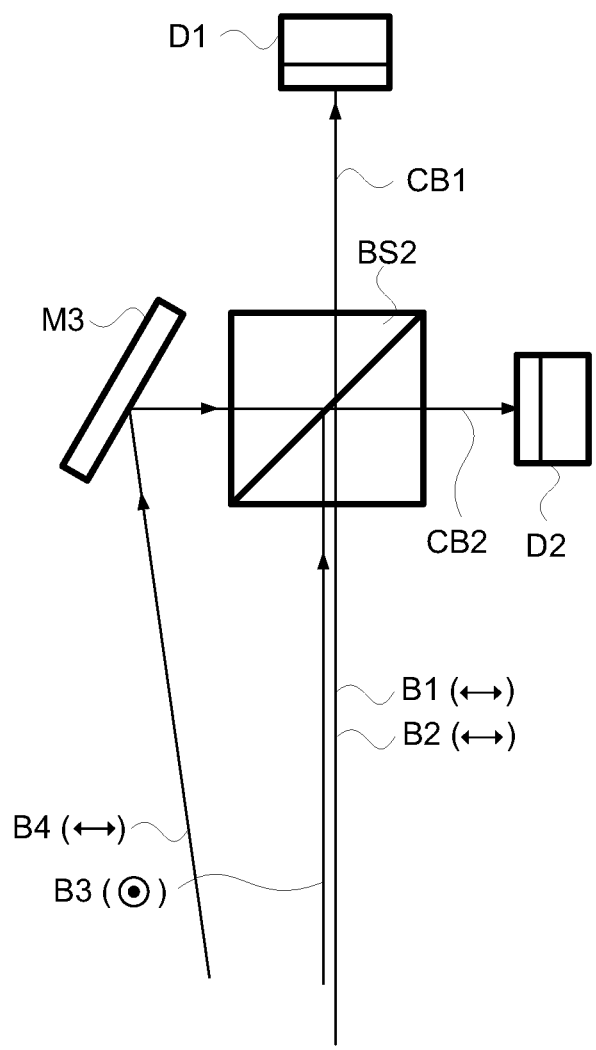
FIG. 6 illustrates an exemplary polarization differentiation technique applied to an arrangement of the refractive index measuring apparatus in accordance with the present invention.

FIG. 6 illustrates an arrangement of apparatus 100 in which polarization differentiation can be used to ensure that the interfering beams are probing substantially the same area of the sample 20. Specifically, as illustrated in FIG. 6, the first beam B1, the second beam B2 and the fourth beam B4 are parallel polarized, and the third beam B3 is perpendicularly polarized. This polarization state can be introduced by inserting a quarter waveplate between sample 20 and mirror M1; and between beam splitter BS1 and mirror M2 (see FIG. 1); and a half waveplate between beam splitter BS1 and M3 (see FIG. 6). In addition, beam splitter BS2 should be a polarized beam splitter. In this manner, beam splitter BS2 can pass the parallel polarized first and second beams (B1 B2) towards detector D1 with minimal losses, and effectively combine and guide the perpendicularly polarized third beam B3 and parallel polarized fourth beam B4 towards detector D2. Since the two combined beams CB1 and CB2 are separated by the polarized beam splitter BS2, CB1 and CB2 do not need to be separated spatially before the polarized beam splitter BS2. Therefore, when using polarization differentiation, the third beam B3 and the first beam B1 can overlap physically and do not need to be walked off from each other.

In the arrangements described thus far, it has been shown that an absolute refractive index can be easily measured with high accuracy using any of the arrangements of apparatus 100. However, the present invention is not limited to the measuring of the refractive index. Indeed, if the light source 10 of apparatus 100 includes multiple light emitting elements, such as laser sources LS1, LS2 . . . and LSN as shown in FIG. 4, each light source can be used to measure a number of fringes at a difference wavelength from which the refractive index of the sample can be calculated at different wavelengths. Alternatively, the refractive index of a sample can be measured with different wavelengths as different times, and the results of the measured refractive index can be used to calculate the Abbe number. Thus, apparatus 100 can also be used to measure the Abbe number of sample 20.

More specifically, as it is known to persons having ordinary skill in the art, when light passes through a lens and gets dispersed, light with shorter wavelengths travels more slowly than light with longer wavelengths. The value, or amount, of dispersion depends on the refractive index of the material. Incidentally, this value is sometimes referred to as refractive efficiency, constringence, V-number or Abbe number. Therefore, using at least one of the arrangements described above, the Abbe number can be calculated as follows. The measured refractive index using this invention with one light source with a wavelength $\lambda$ is the refractive index of the sample at that particular wavelength $\lambda$. When multiple light sources are used, the sample refractive indices can be measured at those wavelengths afforded by those light sources. Therefore, the refractive indices, $n_d$, $n_F$, and $n_C$ can be measured at $\lambda$=587.56 nm (d-line), 486.13 nm (F-line), 656.27 nm (C-line), respectively. The Abbe number (with respect to the yellow Fraunhofer d-line at 587.56 nm wavelength) can be calculated using $V_d = (n_d - 1)/(n_F - n_C)$. The other Abbe numbers with respect to the F and C lines can be obtained in a similar manner. In addition, the Abbe number with respect to the green mercury e-line ($\lambda$=546.073 nm) can be calculated using $V_e = (n_e - 1)/(n_{F'} - n_{C'})$ with e line (546.07 nm), F' line (479.99 nm), and C' line (643.85 nm). Thus, an Abbe number of the material of a given sample can be determined by calculating refractive indices of such a material with respect to a d-line wavelength (587.56 nm), a F-line wavelength (486.13 nm) and C-line wavelength (656.27 nm) using Eq. (4). Similar calculations can be done for refractive indices with respect to the green mercury e-line wavelength (546.073 nm), and other definitions of Abbe number.

<Exemplary Method>

Figure 7:
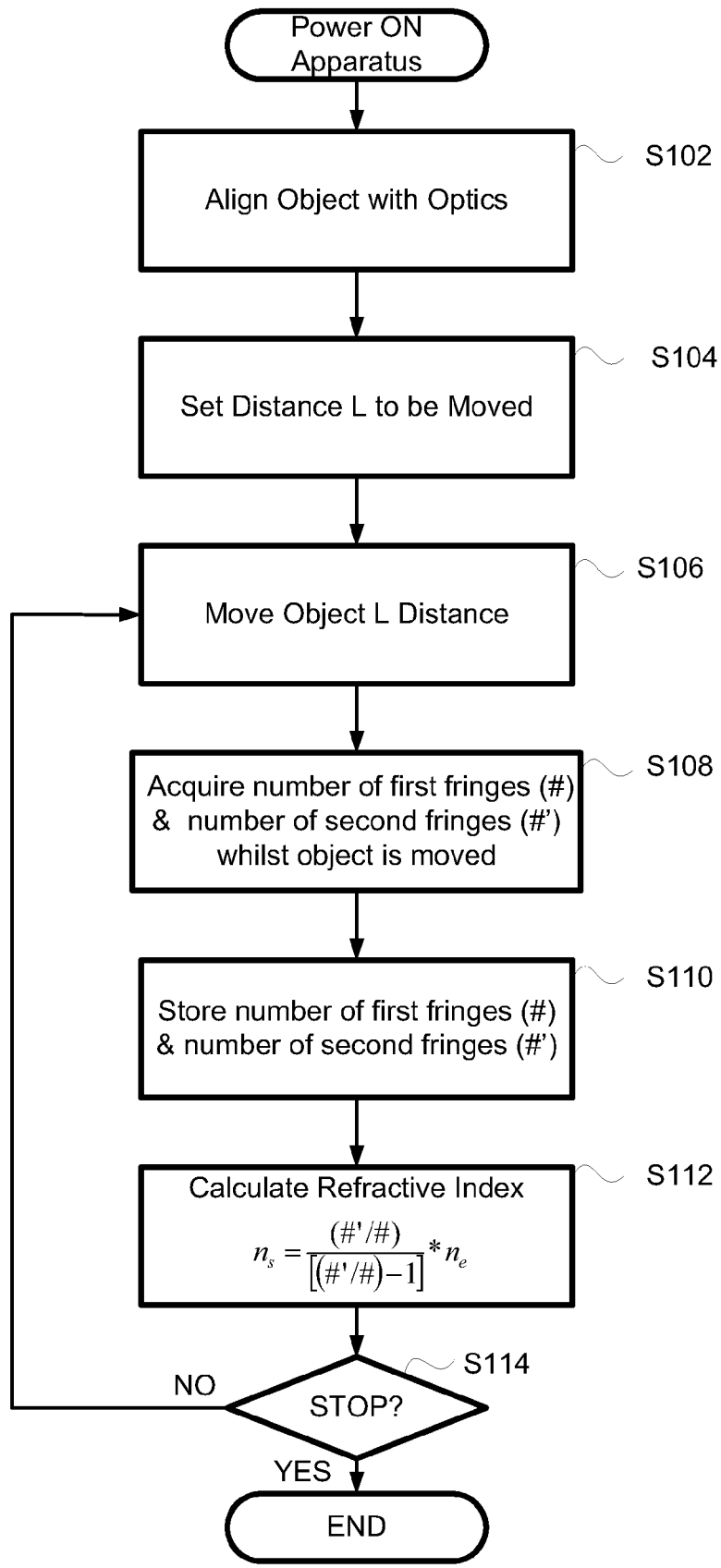
FIG. 7 illustrates a flowchart with exemplary process steps of a measuring method performed by the refractive index measuring apparatus in accordance with the present invention

Next, a method for performing a measurement using any of the arrangements of apparatus 100 set forth above will be described with reference to the flowchart of FIG. 7. The process steps of FIG. 7 can be performed by the analyzer 115 and/or the processing device 120 (shown in FIG. 1). Accordingly, in order to start the measurement process, the apparatus is first powered ON. Powering ON the apparatus may include, for example, activating the light source light of a predetermined wavelength or wavelengths, and placing the sample or object in the signal arm of the interferometer 110. Then, in step S102, an alignment routine is performed to align the sample with the optics of interferometer 110. For example, it may be desirable to ensure that each of the detectors D1 and D2 is able to receive a signal from the light source 10. In order to perform an alignment routine, an alignment command may be entered, for example, via a graphical user interface (GUI) or a user input unit (e.g., a mouse) of processing device 120.

At step S104, still interacting via a GUI or user input unit, the distance L that the sample will be moved for each measurement is entered. It should be noted that, as stated above, the number of first fringes and the number of second fringes are repeatedly obtained while the sample is moved by a distance L. Thus, in order to ensure a high degree of accuracy and to minimize uncertainties, the sample is to be advanced preferably in steps of a relatively small distance L.

At step S106, once the apparatus 100 has been aligned and all of the required parameters have been entered, a measurement routine that includes steps S106 to S114 is started by activating the moving means, such as a micrometer step-motor or any device that changes the position of the object with respect to the incident beam or beams. That is, at step S106 the sample or object is set in movement. While the object is moved, an optical path difference (and therefore a phase delay) is introduced to the first beam B1 with respect to the second beam B2, and to the fourth beam B4 with respect to the third beam B3.

The optical path difference introduced to each of first beam B1 and fourth beam B4 causes that the first fringes and second fringes be detected at detector D1 and detector D2, respectively. In turn, in step S108, the processing device 120 acquires, via the analyzer 115, a number of first fringes (#) and a number of second fringes (#'). For convenience and ease of calculation, it may be preferable to stop fringe counting at some integer number of fringes. However, for purposes of accuracy, it may be more advantageous to stop fringe counting with at least one decimal fraction beyond an integer count, as discussed more in detail below with reference to FIG. 11. In step S110, the acquired number of first fringes and number of second fringes are stored. Given the processing speed of current data processing devices and due to the simplicity of Eq. (4), it is entirely feasible that, at step S112, the processing device 120 may immediately calculate the refractive index of the sample and continuously display the calculation result, for example, on a display unit of the processing device 120. The process flow then advances to step S114 and automatically returns to step S106 (NO in S114), unless a stop input (YES in S114) is entered, e.g., by a user, or until a predetermined length of the sample 20 has been moved in increments of distance L. Here, it should be noted that steps S112 and S114 can be interchanged, and the calculation of the refractive index can take place after the measurement routine is completed. In order to calculate the Abbe number of a given sample, the flow process of FIG. 7 can be repeated as necessary to measure the refractive indices of the sample at different wavelengths using Eq. (4). For example, the Abbe number of the material of a given sample can be determined by calculating refractive indices of such a material with respect to a d-line wavelength (587.56 nm), a F-line wavelength (486.13 nm) and C-line wavelength (656.27 nm) using Eq. (4) to determined the indices of the sample at each of the d-line, F-line and C-line wavelengths. Then the Abbe number can be calculated (with respect to the yellow Fraunhofer d-line at 587.56 nm wavelength) $V_d=(n_d-1)/(n_F-n_C)$; and other Abbe numbers with respect to the F and C lines can be obtained in a similar manner.

<Experimental Data>

Next, a brief description of measurement results is presented with reference to FIG. 8 through FIG. 11. First, it is noted that any of the arrangements of apparatus 100 and the measurement method can be applied to a solid sample or to a liquid sample in a container. For purposes of obtaining the following experimental data, liquid samples in a wedged shape container have been used.

Figures 8, 9:
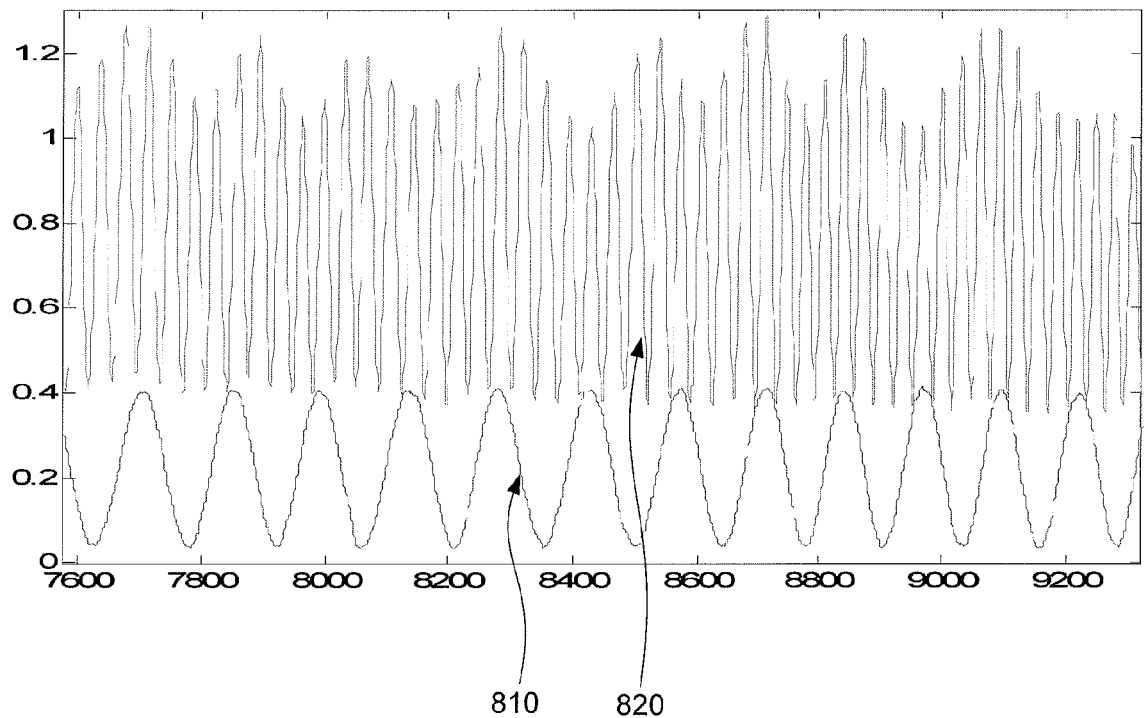
FIG. 8 illustrates a graph with experimental results of two simultaneous measurements to obtain a number of first fringes and a number of second fringes.
FIG. 9 illustrates exemplary measurement results including a number of first fringes, and a number of second fringes, and a refractive index calculated based on the numbers of first and second fringes.

FIG. 8 illustrates a graph with experimental results of two simultaneous measurements to obtain a number of first fringes (#) and a number of second fringes (#'). In FIG. 8, the abscissa represents the number of fringes (indicated in data points) and the ordinate represents the intensity (or height) of the fringes, in arbitrary units, as observed in analyzer 115. The bottom signal represents fringes detected by detector D1 (i.e., the number of first fringes 810). The top signal represents fringes detected by detector D2 (i.e., the number of second fringes 820). As shown in FIG. 8, both measurements were taken concurrently and both are probing the same area of the sample simultaneously. The refractive index of the liquid, deionized (DI) water in this case, has been calculated using Eq. (4). Results of the measurements are tabulated in the table of FIG. 9.

FIG. 9 illustrates tabulated exemplary measurement results including a number of first fringes, and a number of second fringes, and a refractive index calculated based on the numbers of first and second fringes. Specifically, the number of first fringes (#) and the number of second fringes (#') were obtained by illuminating a transparent cell containing DI water with a first light source (e.g., a first HeNe laser emitting at 632 nm). The same sample was then illuminated with a second light source (e.g., a second HeNe laser emitting at 543 nm). In both instances, the fringes were obtained while the transparent liquid cell was translated in steps of 200 μm by about 1 mm. The resultant average absolute refractive index at the first wavelength of 632 nm is 1.32832, while at the second wavelength of 543 nm is 1.33114. These values compare well with the standard refractive index value of approximately 1.333 for commercial DI water. Although specific data indicative of wavelengths, step size and translation length are discussed above, it should be noted that is not critical to know the exact amount of travel or step size. The precise count of the first and second fringes will yield increasingly accurate results by simply increasing the number of fringes counted (see discussion below in reference to FIG. 11).

Figure 10A:
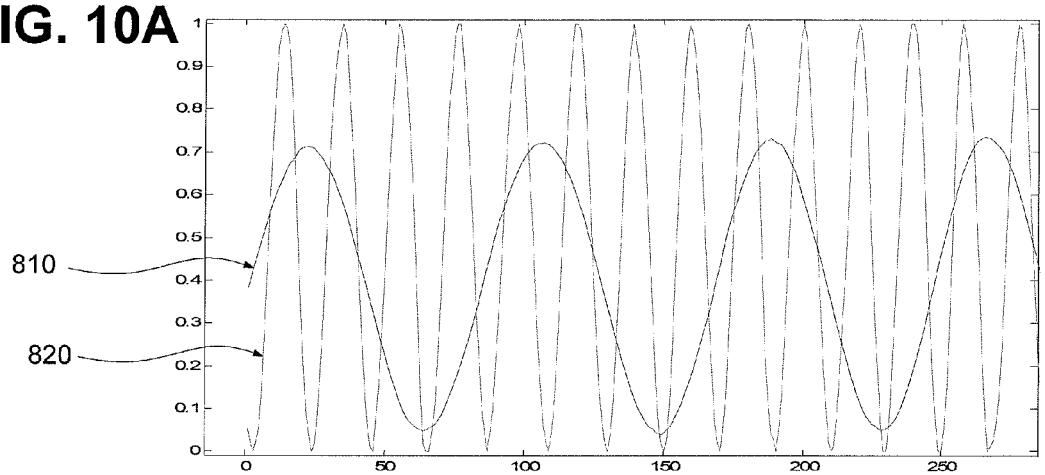
FIGS. 10A through 10C illustrate a time-series of graphs corresponding to two simultaneous measurements to obtain a number of first fringes and a number of second fringes.
Figure 10B:
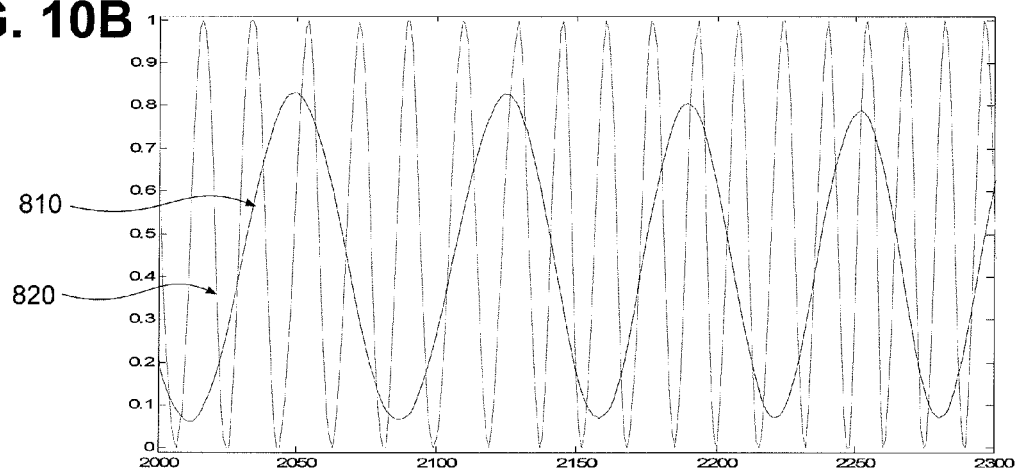
Figure 10C:
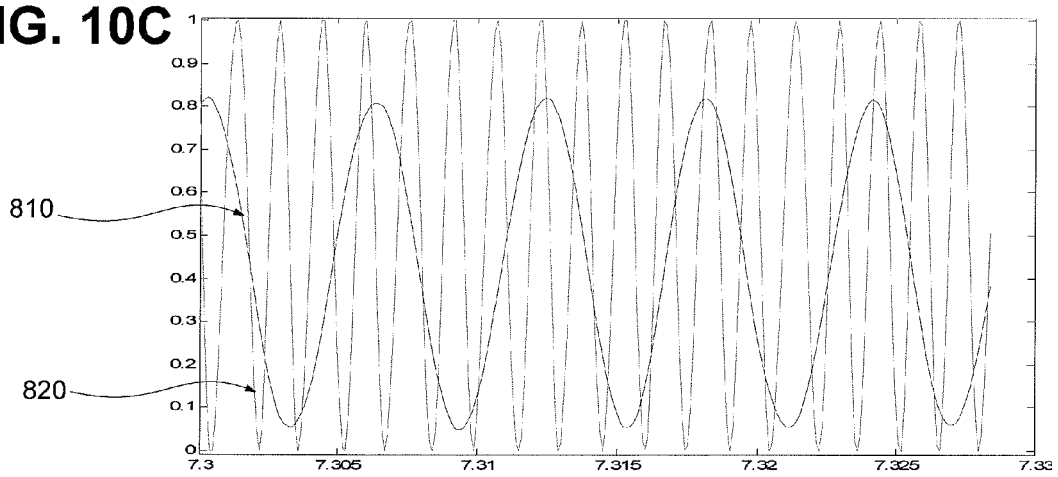

FIGS. 10A through 10C illustrate a time-series of graphs corresponding to two simultaneous measurements to obtain a number of first fringes 810 and a number of second fringes 820. In principle, each of the three sections illustrated in FIGS. 10A through 10C, respectively, can be used to calculate the sample refractive index, $n_s$, using Eq. (4). Therefore, the ratio between the number of first fringes and the number of the second fringes should be constant if the sample refractive index, $n_s$, is homogeneous. This fact does not depend on the speed or the amount of the sample movement. Therefore, the measured results are very robust and do not depend on the step size or the amount of the sample translation.

Although the measured results should be constant regardless of the amount of the sample movement, the accuracy of the measurement can be linearly improved by increasing the number of fringes counted, and/or averaging several sets of data for the numbers of first and second fringes. This is because the uncertainty in counting the number of fringes is less than one, while the number of fringes is proportional to the amount of the sample translation. FIG. 11 illustrates an exemplary summary of experimental results obtained with a refractive index measuring method and apparatus in accordance with the present invention. As tabulated in FIG. 11, five runs (Runs 1-5) have been averaged to obtain the "mean" and standard deviation (sigma) when the number of first fringes is counted to 100 and 1000, respectively.

As it can be appreciated from FIG. 11, when the number of first fringes # is increased from 100 to 1000 (e.g., by translating the sample 10 times longer), the uncertainty of the measurement (characterized by sigma) is reduced by about 10 times (from 0.0004 to 0.00005). Moreover, it is also evidenced that the accuracy of the measurements can be further improved when the number of fringes is counted to one digit after the decimal point. That is, if the number of second fringes 820 (see FIG. 8) is counted taking into account the phase difference with respect to the number of first fringes 810, the number of second fringes can be counted to one or more digits after the decimal point. In this manner, as shown in FIG. 11, an improvement by a factor of 5 (i.e., sigma is reduced from 0.00005 to 0000.1) is demonstrated when the number of second fringes #' is counted to one digit after the decimal point. In other words, it should be noted that the sigma, which is indicative of measurement uncertainty is improved with higher number of fringes counted. This can be achieved by moving the sample with a longer distance or having the sample with a larger wedge angle. Thus, the improvement of the measurement accuracy is not fundamentally limited. That is, by increasing the number of fringes counted, the accuracy of the measurement can be extremely high. In particular, the sigma can be further improved by counting fringes to one digit after the decimal point.

From the foregoing detailed description and exemplary experimental results, it will be evident to persons having ordinary skill in the art that the simplicity of the disclosed technique presents some remarkable advantages over other techniques currently proposed in theory or commercially available in the marketplace. Advantageously, with the method and apparatus disclosed herein, an absolute refractive index can be measured in an accurate and simple manner because the disclosed technique uses a "reference-less" approach. In addition, since the concurrent measurements to obtain the first number of fringes # and second number of fringes #' can be improved simply by increasing the number of counts (i.e., the number of counted fringes), the accuracy of the disclosed technique can be very high. The only measurement uncertainty that may influence the accuracy of the measurement mainly comes from the uncertainty in counting the number of first and second fringes. This uncertainty can be minimized by counting more fringes which can be readily achieved by using a larger sample size or larger wedge angle in the sample. There is no stringent signal-to-noise (S/N) requirement on the detector(s) as long as the fringes are visible. In contrast to known conventional techniques, there is also no complicated formulas or lengthy algorithms that need to be solved and processed. For example, in certain conventional techniques, the fringe shape is important since a fitting (between simulated and measured results) is performed to extract (estimate) the refractive index of a sample. In other techniques, the contrast ratio can only be measured if the heights of "peaks and valleys" can be measured accurately. The technique of the present invention overcomes both of these constraints because, when the two measurements are carried concurrently and under the same conditions, there is no need to compare simulated and measured results. In addition, as long as the fringes can be accurately counted, there is no need for high signal-to-noise or contrast ratios. Moreover, any uncertainty or inaccuracies that may be introduced by fringe counting can be minimized by increasing the counting. In addition to these, when the light source consists of multiple lasers with suitable wavelengths the Abbe number can also be measured accurately.

Modifications

The above-described embodiments and exemplary experimental data are premised on the assumption that a wedge-shaped sample has been measured. However, the scope of the present invention can also be extended to other shapes of samples, such as thin films or flowing liquids. Specifically, as evidenced above, since the sole constraint for measuring the refractive index is the accurate counting of first and second fringes, such fringes can be formed even if the sample is not wedge-shaped. For example, a parallel sample having even microscopic morphological variations on its surface may very well generate the first and second fringes, as described above. It is, therefore, entirely feasible that the above describe embodiments can be applied not only to measuring the refractive index and Abbe number, but also morphological variations and thickness of a sample.

Those skilled in the art will appreciate that many variations are possible within the scope of the examples described herein. Thus, while the features of the invention have been described with reference to particular embodiments, it will be understood that structural and functional modifications may be made without departing from the scope of the following claims.

The invention claimed is:

1. A method for measuring refractive index of an object, comprising:
    acquiring a number of first fringes of a first interference pattern formed by interference of a first beam of light transmitted through the object with a second beam of light not transmitted through the object;
    acquiring a number of second fringes of a second interference pattern formed by interference of a third beam of light reflected from a first surface of the object with a fourth beam of light transmitted through the object and reflected from a second surface of the object; and
    calculating the refractive index of the object based on the number of first fringes and the number of second fringes,
    wherein the calculating step includes obtaining a radio of the number of second fringes divided by a difference of the number of second fringes minus the number of first fringes.

2. The method according to claim 1, wherein acquiring the number of first fringes and acquiring the number of second fringes is performed simultaneously while the object is moved with respect to the first, third and fourth beams.

3. The method according to claim 1, further comprising moving the object a predetermined distance in a direction orthogonal to the first beam,
    wherein acquiring the number of first fringes and acquiring the number of second fringes is performed while the object is moved.

4. The method according to claim 1, wherein acquiring the number of first fringes and acquiring the number of second fringes includes detecting the number of first fringes at a first detector concurrently with detecting the number of second fringes at a second detector while the object is moved with respect to the first, third and fourth beams.

5. The method according to claim 1, further comprising moving the first beam a predetermined distance in a direction orthogonal to the object,
    wherein acquiring the number of first fringes and acquiring the number of second fringes is performed while the first beam is moved.

6. The method according to claim 1, wherein acquiring the number of first fringes and acquiring the number of second fringes includes detecting the number of first fringes at a first detector concurrently with detecting the number of second fringes at a second detector while the first, third and fourth beams are moved in an orthogonal direction with respect to the object.

7. The method according to claim 1, wherein the object is a solid having a wedged shape or a liquid contained in a wedge-shaped container.

8. The method according to claim 7, wherein the first surface is not parallel to the second surface of the object, and
    wherein a distance between the first surface and the second surface of the object is variable along a predetermined length of the object.

9. A method for measuring refractive index of an object, comprising:
   acquiring a number of first fringes of a first interference pattern formed by interference of a first beam of light transmitted through the object with a second beam of light not transmitted through the object;
   acquiring a number of second fringes of a second interference pattern formed by interference of a third beam of light reflected from a first surface of the object with a fourth beam of light transmitted through the object and reflected from a second surface of the object; and
   calculating the refractive index of the object based on the number of first fringes and the number of second fringes, wherein the calculating step includes resolving the following expression:

$$n_s = \frac{(\#'/\#)}{[(\#'/\#) - 1]} * n_e$$

where $n_s$ the refractive index of the object, $n_e$ is the refractive index of the environment in which the object is in, and #' is the number of second fringes, and # is the number of first fringes.

10. The method according to claim 9, further comprising:
   determining an Abbe number of the object by calculating refractive indices of the a material of the object with respect to a d-line wavelength (587.56 nm), a F-line wavelength (486.13 nm) and C-line wavelength (656.27 nm) using the expression $$n_s = \frac{(\#'/\#)}{[(\#'/\#) - 1]} * n_e$$

wherein the refractive index $n_s$ calculated for each of the d-line, F-line and C-line wavelengths.

11. A method for measuring refractive index of an object, comprising:
   generating a first beam of light having a first optical path and a second beam of light having a second optical path different from the first optical path;
   placing the object in one of the first and second optical paths such that a portion of the first or second optical path passes through the object;
   combining the first beam and the second beam to form a first interference pattern;
   generating a third beam of light and a fourth beam of light;
   reflecting the third beam from a first surface of the object so as to form a third optical path;
   transmitting the fourth beam through the object and reflecting the fourth beam from a second surface of the object so as to form a fourth optical path;
   combining the third and fourth beams to form a second interference pattern;
   counting a number of first fringes of the first interference pattern and a number of second fringes of the second interference pattern; and
   calculating the refractive index of the object based on the number of first fringes and the number of second fringes, wherein the calculating step includes resolving the following expression $$n_s = \frac{(\#'/\#)}{[(\#'/\#) - 1]} * n_e$$

where $n_s$ is the refractive index of the object, $n_e$ is the refractive index of the environment in which the object is in, and #' is the number of second fringes, and # is the number of first fringes.

12. The method according to claim 11, further comprising moving the object in a direction substantially orthogonal to the third and fourth beams, and moving the object in a direction substantially orthogonal to the one of the first and second beams while counting the number of first and second fringes.

13. The method according to claim 11, wherein the portion of the first or second optical path that passes through the object is substantially equal to a distance that a corresponding one of the first and second beams travels through the object.

14. The method according to claim 13, wherein the fourth beam travels through the object a distance substantially equal to the distance that the one of the first and second beams travels through the object.

15. The method according to claim 14, further comprising varying the distance that the one of the first and second beams travels through the object while counting the number of first and second fringes.

16. The method according to claim 11, further comprising varying the length of the portion of the first or second optical path that passes through the object or varying the distance that the fourth beam travels through the object while counting the number of first and second fringes.

17. The method according to claim 11, further comprising:
   determining an Abbe number of the object by calculating refractive indices of the object with respect to a d-line wavelength (587.56 nm), a F-line wavelength (486.13 nm) and C-line wavelength (656.27 nm) using the expression $$n_s = \frac{(\#'/\#)}{[(\#'/\#) - 1]} * n_e$$

wherein the refractive index $n_s$ is calculated for each of the d-line, F-line and C-line wavelengths.

18. The method according to claim 11, wherein acquiring the number of first fringes and acquiring the number of second fringes is performed simultaneously while the object is moved with respect to the first, third and fourth beams.

19. An apparatus for measuring the refractive index of an object, comprising:
   a light source that generates light to form a first, second, third and fourth beams, the first beam having a first optical path and the second beam having a second optical path different from the first optical path;
   an object holder that holds the object in one of the first and second optical paths such that a portion of the first or second optical path passes through the object;
   a first optical combiner that combines the first beam and the second beam to form a first interference pattern;
   a second optical combiner that combines the third and fourth beams to form a second interference pattern;
   a fringe counter that counts a number of first fringes of the first interference pattern and a number of second fringes of the second interference pattern; and a calculating device that calculates the refractive index of the object based on the number of first fringes and the number of second fringes, wherein the second optical combiner combines the third and fourth beams after the third beam is reflected from a first surface of the object without being transmitted through the object, and after the fourth beam is transmitted through the object and reflected from a second surface of the object, and wherein the calculating device calculates the refractive index of the object by solving the following expression:

$$n_s = \frac{(\#'/\#)}{[(\#'/\#)-1]} * n_e$$

where $n_s$ is the refractive index of the object, $n_e$ is the refractive index of the environment in which the object is in, and $\#'$ is the number of second fringes, and $\#$ is the number of first fringes.

20. The apparatus according to claim 19, wherein the calculating device further calculates an Abbe number of the object by calculating refractive indices of the a material of the object with respect to a d-line wavelength (587.56 nm), a F-line wavelength (486.13 nm) and C-line wavelength (656.27 nm) using the expression $$n_s = \frac{(\#'/\#)}{[(\#'/\#)-1]} * n_e$$

wherein $n_s$ is calculated for each of the d-line, F-line and C-line wavelengths.

21. The apparatus according to claim 19, further comprising moving means for moving the object a predetermined distance in a direction substantially orthogonal to the first beam, wherein the fringe counter counts the number of first fringes and the number of second fringes while the object is moved by the moving means.

22. The apparatus according to claim 19, further comprising a first detector and a second detector, wherein the first detector detects the first interference pattern substantially simultaneously when the second detector detects the second interference pattern while the object is moved.

23. The apparatus according to claim 19, wherein the light source includes a plurality of light sources, each of the light sources having a different wavelength.

* * * * *